(12) United States Patent
Geraghty et al.

(10) Patent No.: US 8,048,156 B2
(45) Date of Patent: Nov. 1, 2011

(54) MULTIFOCAL ACCOMMODATING INTRAOCULAR LENS

(75) Inventors: Edward Geraghty, Rancho Santa Margarita, CA (US); Daniel G. Brady, San Juan Capistrano, CA (US); Timothy R. Bumbalough, Fullerton, CA (US); Douglas S. Cali, Mission Viejo, CA (US)

(73) Assignee: Abbott Medical Optics Inc., Santa Ana, CA (US)

( * ) Notice: Subject to any disclaimer, the term of this patent is extended or adjusted under 35 U.S.C. 154(b) by 191 days.

(21) Appl. No.: 11/966,365

(22) Filed: Dec. 28, 2007

(65) Prior Publication Data
US 2009/0012609 A1    Jan. 8, 2009

Related U.S. Application Data

(60) Provisional application No. 60/882,839, filed on Dec. 29, 2006.

(51) Int. Cl.
*A61F 2/16* (2006.01)
(52) U.S. Cl. .................. 623/6.37; 623/6.49; 623/6.4
(58) Field of Classification Search ............ 623/6.11, 623/6.38, 6.39, 6.4, 6.27, 6.43
See application file for complete search history.

(56) References Cited

U.S. PATENT DOCUMENTS

| | | |
|---|---|---|
| 1,483,509 A | 2/1924 | Bugbee |
| 2,129,305 A | 9/1938 | Feinbloom |
| 2,274,142 A | 2/1942 | Houchin |
| 2,405,989 A | 6/1946 | Beach |
| 2,511,517 A | 6/1950 | Spiegel |
| 2,834,023 A | 5/1958 | Lieb |
| 3,004,470 A | 10/1961 | Ruhle |
| 3,031,927 A | 5/1962 | Wesley |
| 3,034,403 A | 5/1962 | Neefe |
| RE25,286 E | 11/1962 | DeCarle |
| 3,210,894 A | 10/1965 | Bentley et al. |
| 3,227,507 A | 1/1966 | Feinbloom |

(Continued)

FOREIGN PATENT DOCUMENTS

AU    3225789    10/1989

(Continued)

OTHER PUBLICATIONS

U.S. Appl. No. 10/280,918, filed Aug. 5, 2003.

(Continued)

*Primary Examiner* — David H Willse
*Assistant Examiner* — Tiffany Shipmon (57) ABSTRACT

An intraocular lens for providing accommodative visions to a subject includes an adjustable optic and a haptic that is operably coupled to the optic. The adjustable optic comprises an optical axis, a central zone disposed about the optical axis, and an annular zone surrounding the central zone. The optic may also comprise additional annular zones disposed about the central zone and the first annular zone. The haptic comprises a transparent portion protruding into the adjustable optic. The intraocular lens has a disaccommodative configuration in which the central zone has a base optical power and an accommodative configuration in which the central zone has an add optical power that is at least about 1 Diopter greater than the base optical power, preferably at least about 2 Diopters greater than the base optical power. In some embodiments, the add optical power is at least 3 Diopters, or even 4 Diopters, greater than the base optical power. The central zone and the annular zone have different optical powers when the adjustable intraocular lens is in the accommodative configuration and/or when the adjustable intraocular lens is in the disaccommodative configuration.

36 Claims, 6 Drawing Sheets

U.S. PATENT DOCUMENTS

| | | |
|---|---|---|
| 3,339,997 A | 9/1967 | Wesley |
| 3,420,006 A | 1/1969 | Barnett |
| 3,431,327 A | 3/1969 | Tsuetaki |
| 3,482,906 A | 12/1969 | Volk |
| 3,542,461 A | 11/1970 | Girard et al. |
| 3,673,616 A | 7/1972 | Fedorov et al. |
| 3,693,301 A | 9/1972 | Lemaitre |
| 3,711,870 A | 1/1973 | Deitrick |
| 3,718,870 A | 2/1973 | Keller |
| 3,794,414 A | 2/1974 | Wesley |
| 3,866,249 A | 2/1975 | Flom |
| 3,906,551 A | 9/1975 | Otter |
| 3,913,148 A | 10/1975 | Potthast |
| 3,922,728 A | 12/1975 | Krasnov |
| 3,925,825 A | 12/1975 | Richards et al. |
| 3,932,148 A | 1/1976 | Krewalk, Sr. |
| 4,010,496 A | 3/1977 | Neefe |
| 4,014,049 A | 3/1977 | Richards et al. |
| 4,041,552 A | 8/1977 | Ganias |
| 4,053,953 A | 10/1977 | Flom et al. |
| 4,055,378 A | 10/1977 | Feneberg et al. |
| 4,056,855 A | 11/1977 | Kelman |
| 4,062,629 A | 12/1977 | Winthrop |
| 4,073,579 A | 2/1978 | Deeg et al. |
| 4,074,368 A | 2/1978 | Levy, Jr. et al. |
| 4,087,866 A | 5/1978 | Choyce et al. |
| 4,110,848 A | 9/1978 | Jensen |
| 4,159,546 A | 7/1979 | Shearing |
| 4,162,122 A | 7/1979 | Cohen |
| 4,195,919 A | 4/1980 | Shelton |
| 4,199,231 A | 4/1980 | Evans |
| 4,210,391 A | 7/1980 | Cohen |
| 4,240,719 A | 12/1980 | Guilino et al. |
| 4,244,060 A | 1/1981 | Hoffer |
| 4,244,597 A | 1/1981 | Dandle |
| 4,251,887 A | 2/1981 | Anis |
| 4,253,199 A | 3/1981 | Banko |
| 4,254,509 A | 3/1981 | Tennant |
| 4,261,065 A | 4/1981 | Tennant |
| 4,274,717 A | 6/1981 | Davenport |
| 4,285,072 A | 8/1981 | Morcher et al. |
| 4,298,994 A | 11/1981 | Clayman |
| 4,307,945 A | 12/1981 | Kitchen et al. |
| 4,315,336 A | 2/1982 | Poler |
| 4,315,673 A | 2/1982 | Guilino et al. |
| 4,316,293 A | 2/1982 | Bayers |
| 4,338,005 A | 7/1982 | Cohen |
| 4,340,283 A | 7/1982 | Cohen |
| 4,340,979 A | 7/1982 | Kelman |
| 4,361,913 A | 12/1982 | Streck |
| 4,370,760 A | 2/1983 | Kelman |
| 4,373,218 A | 2/1983 | Schachar |
| 4,377,329 A | 3/1983 | Poler |
| 4,377,873 A | 3/1983 | Reichert, Jr. |
| 4,402,579 A | 9/1983 | Poler |
| 4,404,694 A | 9/1983 | Kelman |
| 4,409,691 A | 10/1983 | Levy |
| 4,418,991 A | 12/1983 | Breger |
| 4,424,597 A | 1/1984 | Schlegel |
| 4,442,553 A | 4/1984 | Hessburg |
| 4,463,458 A | 8/1984 | Seidner |
| 4,476,591 A | 10/1984 | Arnott |
| 4,504,981 A | 3/1985 | Walman |
| 4,504,982 A | 3/1985 | Burk |
| 4,512,040 A | 4/1985 | McClure |
| 4,551,864 A | 11/1985 | Akhavi |
| 4,560,383 A | 12/1985 | Leiske |
| 4,562,600 A | 1/1986 | Ginsberg et al. |
| 4,573,775 A | 3/1986 | Bayshore |
| 4,573,998 A | 3/1986 | Mazzocco |
| 4,575,878 A | 3/1986 | Dubroff |
| 4,580,882 A | 4/1986 | Nuchman et al. |
| 4,581,033 A | 4/1986 | Callahan |
| 4,596,578 A | 6/1986 | Kelman |
| 4,615,701 A | 10/1986 | Woods |
| 4,617,023 A | 10/1986 | Peyman |
| 4,618,228 A | 10/1986 | Baron et al. |
| 4,618,229 A | 10/1986 | Jacobstein et al. |
| 4,629,460 A | 12/1986 | Dyer |
| 4,636,049 A | 1/1987 | Blaker |
| 4,636,211 A * | 1/1987 | Nielsen et al. ............... 623/6.28 |
| 4,637,697 A | 1/1987 | Freeman |
| 4,641,934 A | 2/1987 | Freeman |
| 4,661,108 A | 4/1987 | Grendahl et al. |
| 4,664,666 A | 5/1987 | Barrett |
| 4,676,792 A | 6/1987 | Praeger |
| 4,687,484 A | 8/1987 | Kaplan |
| 4,693,572 A | 9/1987 | Tsnetaki et al. |
| 4,693,716 A | 9/1987 | Mackool |
| RE32,525 E | 10/1987 | Pannu |
| 4,702,244 A | 10/1987 | Mazzocco |
| 4,704,016 A | 11/1987 | DeCarle |
| 4,710,194 A | 12/1987 | Kelman |
| 4,720,286 A | 1/1988 | Bailey et al. |
| 4,725,278 A | 2/1988 | Shearing |
| 4,731,078 A | 3/1988 | Stoy et al. |
| 4,737,322 A | 4/1988 | Bruns et al. |
| 4,752,123 A | 6/1988 | Blaker |
| 4,759,762 A | 7/1988 | Grendahl |
| 4,769,033 A | 9/1988 | Nordan |
| 4,769,035 A | 9/1988 | Kelman |
| 4,787,903 A | 11/1988 | Grendahl |
| 4,790,847 A | 12/1988 | Woods |
| 4,813,955 A | 3/1989 | Achatz et al. |
| 4,816,032 A | 3/1989 | Hetland |
| 4,830,481 A | 5/1989 | Futhey et al. |
| 4,840,627 A | 6/1989 | Blumenthal |
| 4,842,601 A | 6/1989 | Smith |
| 4,878,910 A | 11/1989 | Koziol et al. |
| 4,878,911 A | 11/1989 | Anis |
| 4,881,804 A | 11/1989 | Cohen |
| 4,888,012 A | 12/1989 | Horn et al. |
| 4,888,015 A | 12/1989 | Domino |
| 4,888,016 A | 12/1989 | Langerman |
| 4,890,912 A | 1/1990 | Visser |
| 4,890,913 A | 1/1990 | DeCarle |
| 4,892,543 A | 1/1990 | Turley |
| 4,898,461 A | 2/1990 | Portney |
| 4,906,246 A | 3/1990 | Grendahl |
| 4,917,681 A | 4/1990 | Nordan |
| 4,919,663 A | 4/1990 | Grendahl |
| 4,921,496 A | 5/1990 | Grendahl |
| 4,923,296 A | 5/1990 | Erickson |
| 4,932,966 A | 6/1990 | Christie et al. |
| 4,932,968 A * | 6/1990 | Caldwell et al. ............. 623/6.37 |
| 4,938,583 A | 7/1990 | Miller |
| 4,946,469 A | 8/1990 | Sarfarazi |
| 4,955,902 A | 9/1990 | Kelman |
| 4,963,148 A | 10/1990 | Sulc et al. |
| 4,976,534 A | 12/1990 | Milge et al. |
| 4,976,732 A | 12/1990 | Vorosmarthy |
| 4,990,159 A | 2/1991 | Kraff |
| 4,994,058 A | 2/1991 | Raven et al. |
| 4,994,082 A | 2/1991 | Richards et al. |
| 4,994,083 A | 2/1991 | Sulc et al. |
| 5,000,559 A | 3/1991 | Takahashi et al. |
| 5,002,382 A | 3/1991 | Seidner |
| 5,019,098 A | 5/1991 | Mercier |
| 5,019,099 A | 5/1991 | Nordan |
| 5,047,051 A | 9/1991 | Cumming |
| 5,047,052 A | 9/1991 | Dubroff |
| 5,071,432 A | 12/1991 | Baikoff |
| 5,089,024 A | 2/1992 | Christie et al. |
| 5,096,285 A | 3/1992 | Silberman |
| 5,112,351 A | 5/1992 | Christie et al. |
| 5,129,718 A | 7/1992 | Futhey et al. |
| 5,147,397 A | 9/1992 | Christ et al. |
| 5,152,789 A | 10/1992 | Willis |
| 5,158,572 A | 10/1992 | Nielsen |
| 5,166,711 A | 11/1992 | Portney |
| 5,166,712 A | 11/1992 | Portney |
| 5,171,266 A | 12/1992 | Wiley et al. |
| 5,173,723 A | 12/1992 | Volk |
| 5,192,317 A | 3/1993 | Kalb |
| 5,192,318 A | 3/1993 | Schneider |
| 5,201,762 A | 4/1993 | Hauber |
| 5,225,858 A | 7/1993 | Portney |

| Patent Number | Date | Inventor |
|---|---|---|
| 5,258,025 A | 11/1993 | Fedorov et al. |
| 5,260,727 A | 11/1993 | Oksman et al. |
| 5,270,744 A | 12/1993 | Portney |
| 5,275,623 A | 1/1994 | Sarfarazi |
| 5,354,335 A | 10/1994 | Lipshitz et al. |
| RE34,998 E | 7/1995 | Langerman |
| 5,443,506 A | 8/1995 | Carabet |
| 5,476,514 A | 12/1995 | Cumming |
| 5,480,428 A | 1/1996 | Fedorov et al. |
| 5,489,302 A | 2/1996 | Skottun |
| 5,496,366 A | 3/1996 | Cumming |
| 5,521,656 A | 5/1996 | Portney |
| 5,562,731 A | 10/1996 | Cumming |
| 5,574,518 A | 11/1996 | Mercure |
| 5,578,081 A | 11/1996 | McDonald |
| 5,593,436 A | 1/1997 | Langerman |
| 5,607,472 A | 3/1997 | Thompson |
| 5,628,795 A | 5/1997 | Langerman |
| 5,628,796 A | 5/1997 | Suzuki |
| 5,628,797 A | 5/1997 | Richer |
| 5,652,014 A | 7/1997 | Galin et al. |
| 5,652,638 A | 7/1997 | Roffman et al. |
| 5,657,108 A | 8/1997 | Portney |
| 5,674,282 A | 10/1997 | Cumming |
| 5,682,223 A | 10/1997 | Menezes et al. |
| 5,684,560 A | 11/1997 | Roffman et al. |
| 5,766,244 A | 6/1998 | Binder |
| 5,769,890 A | 6/1998 | McDonald |
| 5,776,191 A | 7/1998 | Mazzocco |
| 5,776,192 A | 7/1998 | McDonald |
| 5,814,103 A | 9/1998 | Lipshitz et al. |
| 5,824,074 A | 10/1998 | Koch |
| 5,843,188 A | 12/1998 | McDonald |
| 5,847,802 A | 12/1998 | Meneles et al. |
| 5,876,442 A | 3/1999 | Lipshitz et al. |
| 5,898,473 A | 4/1999 | Seidner et al. |
| 5,968,094 A | 10/1999 | Werblin et al. |
| 5,984,962 A | 11/1999 | Anello et al. |
| 6,013,101 A | 1/2000 | Israel |
| 6,051,024 A | 4/2000 | Cumming |
| 6,083,261 A | 7/2000 | Callahan et al. |
| 6,096,078 A | 8/2000 | McDonald |
| 6,110,202 A | 8/2000 | Barraquer et al. |
| 6,117,171 A | 9/2000 | Skottun |
| 6,120,538 A | 9/2000 | Rizzo, III et al. |
| 6,136,026 A | 10/2000 | Israel |
| 6,152,958 A | 11/2000 | Nordan |
| 6,176,878 B1 | 1/2001 | Gwon et al. |
| 6,197,058 B1 | 3/2001 | Portney |
| 6,197,059 B1 | 3/2001 | Cumming |
| 6,200,342 B1 | 3/2001 | Tassignon |
| 6,217,612 B1 | 4/2001 | Woods |
| 6,228,115 B1 * | 5/2001 | Hoffmann et al. ............ 623/6.49 |
| 6,231,603 B1 | 5/2001 | Lang et al. |
| 6,299,641 B1 | 10/2001 | Woods |
| 6,302,911 B1 | 10/2001 | Hanna |
| 6,322,589 B1 | 11/2001 | Cumming |
| 6,399,734 B1 | 6/2002 | Hodd et al. |
| 6,406,494 B1 | 6/2002 | Laguette et al. |
| 6,443,985 B1 | 9/2002 | Woods |
| 6,485,516 B2 | 11/2002 | Boehm |
| 6,488,708 B2 | 12/2002 | Sarfarazi |
| 6,503,276 B2 | 1/2003 | Lang et al. |
| 6,524,340 B2 | 2/2003 | Israel |
| 6,551,354 B1 | 4/2003 | Ghaziaadeh et al. |
| 6,554,859 B1 | 4/2003 | Lang et al. |
| 6,558,420 B2 | 5/2003 | Green |
| 6,592,621 B1 | 7/2003 | Domino |
| 6,599,317 B1 | 7/2003 | Weinschenk, III et al. |
| 6,616,691 B1 | 9/2003 | Tran |
| 6,616,692 B1 | 9/2003 | Glick et al. |
| 6,638,305 B2 * | 10/2003 | Laguette ................ 623/6.37 |
| 6,638,306 B2 | 10/2003 | Cumming |
| 6,645,246 B1 | 11/2003 | Weinschenk, III et al. |
| 6,660,035 B1 | 12/2003 | Lang et al. |
| 6,749,633 B1 | 6/2004 | Lorenzo et al. |
| 6,749,634 B2 | 6/2004 | Hanna |
| 6,855,164 B2 | 2/2005 | Glazier |
| 6,930,838 B2 | 8/2005 | Schachar |
| 7,018,409 B2 | 3/2006 | Glick et al. |
| 7,025,783 B2 | 4/2006 | Brady et al. |
| 7,097,660 B2 | 8/2006 | Portney |
| 7,125,422 B2 | 10/2006 | Woods |
| 7,150,759 B2 | 12/2006 | Paul et al. |
| 7,179,292 B2 | 2/2007 | Worst et al. |
| 7,220,279 B2 | 5/2007 | Nun |
| 7,223,288 B2 | 5/2007 | Zhang et al. |
| 7,503,938 B2 | 3/2009 | Phillips |
| 2002/0111678 A1 | 8/2002 | Zadno-Azizi et al. |
| 2002/0116058 A1 | 8/2002 | Zadno-Azizi et al. |
| 2002/0120329 A1 | 8/2002 | Lang et al. |
| 2002/0188351 A1 | 12/2002 | Laguette |
| 2003/0004569 A1 | 1/2003 | Haefliger |
| 2003/0060878 A1 | 3/2003 | Shadduck |
| 2003/0060881 A1 | 3/2003 | Glick et al. |
| 2003/0109926 A1 | 6/2003 | Portney |
| 2003/0130732 A1 | 7/2003 | Sarfarazi |
| 2003/0135272 A1 | 7/2003 | Rady et al. |
| 2003/0149480 A1 | 8/2003 | Shadduck |
| 2003/0187505 A1 | 10/2003 | Liao |
| 2003/0204254 A1 | 10/2003 | Peng et al. |
| 2003/0204255 A1 | 10/2003 | Peng et al. |
| 2004/0054408 A1 | 3/2004 | Glick et al. |
| 2004/0082993 A1 | 4/2004 | Woods et al. |
| 2004/0082994 A1 | 4/2004 | Woods et al. |
| 2004/0082995 A1 | 4/2004 | Woods |
| 2004/0111153 A1 | 6/2004 | Woods et al. |
| 2004/0158322 A1 | 8/2004 | Shen |
| 2004/0167621 A1 | 8/2004 | Peyman |
| 2004/0181279 A1 | 9/2004 | Nun |
| 2004/0215340 A1 | 10/2004 | Messner et al. |
| 2005/0018504 A1 | 1/2005 | Marinelli et al. |
| 2005/0021139 A1 | 1/2005 | Shadduck |
| 2005/0027354 A1 | 2/2005 | Brady et al. |
| 2005/0085906 A1 | 4/2005 | Hanna |
| 2005/0085907 A1 | 4/2005 | Hanna |
| 2005/0125057 A1 | 6/2005 | Cumming |
| 2005/0131535 A1 | 6/2005 | Woods |
| 2005/0137703 A1 | 6/2005 | Chen |
| 2005/0288785 A1 | 12/2005 | Portney et al. |
| 2006/0064162 A1 | 3/2006 | Klima |
| 2006/0111776 A1 | 5/2006 | Glick et al. |
| 2006/0116765 A1 | 6/2006 | Blake et al. |
| 2006/0238702 A1 | 10/2006 | Glick et al. |
| 2007/0078515 A1 | 4/2007 | Brady |
| 2007/0100444 A1 * | 5/2007 | Brady et al. ................ 623/6.37 |
| 2007/0106381 A1 | 5/2007 | Blake |
| 2007/0129798 A1 | 6/2007 | Chawdhary |
| 2007/0135915 A1 | 6/2007 | Klima |
| 2007/0213817 A1 | 9/2007 | Esch et al. |
| 2007/0260309 A1 | 11/2007 | Richardson |
| 2007/0299487 A1 | 12/2007 | Shadduck |
| 2008/0161913 A1 | 7/2008 | Brady |
| 2008/0161914 A1 | 7/2008 | Brady |
| 2009/0012609 A1 | 1/2009 | Geraghty |

FOREIGN PATENT DOCUMENTS

| | | |
|---|---|---|
| CH | 681687 | 5/1993 |
| DE | 2702117 | 7/1978 |
| DE | 3246306 | 6/1984 |
| DE | 4038088 | 6/1992 |
| DE | 19501444 | 7/1996 |
| EP | 0064812 | 11/1982 |
| EP | 0246216 | 11/1987 |
| EP | 0328117 | 8/1989 |
| EP | 0329981 | 8/1989 |
| EP | 0337390 | 10/1989 |
| EP | 0342895 | 11/1989 |
| EP | 0351471 | 1/1990 |
| EP | 0356050 | 2/1990 |
| EP | 0488835 | 6/1992 |
| EP | 0507292 | 10/1992 |
| EP | 0566170 | 10/1993 |
| EP | 0601845 | 6/1994 |
| EP | 0691109 | 1/1996 |
| EP | 0897702 | 2/1999 |
| EP | 0766540 | 4/1999 |
| EP | 766540 B1 | 8/1999 |

| | | |
|---|---|---|
| GB | 2058391 | 4/1981 |
| GB | 2124500 | 2/1984 |
| GB | 2129155 | 5/1984 |
| GB | 2146791 | 4/1985 |
| GB | 2192291 | 1/1988 |
| GB | 2215076 | 9/1989 |
| JP | 2126847 A2 | 5/1990 |
| WO | 86/03961 | 7/1986 |
| WO | 87/00299 | 1/1987 |
| WO | 87/07496 | 12/1987 |
| WO | 89/02251 | 3/1989 |
| WO | 89/11672 | 11/1989 |
| WO | 90/00889 | 2/1990 |
| WO | 93/05733 | 4/1993 |
| WO | 94/16648 | 8/1994 |
| WO | 95/03783 | 2/1995 |
| WO | 96/10968 | 4/1996 |
| WO | 96/15734 | 5/1996 |
| WO | 96/25126 | 8/1996 |
| WO | 97/12272 | 4/1997 |
| WO | 97/27825 | 8/1997 |
| WO | 97/43984 | 11/1997 |
| WO | 98/56315 | 12/1998 |
| WO | 00/61036 | 4/2000 |
| WO | 00/27315 | 5/2000 |
| WO | 00/66039 | 11/2000 |
| WO | 01/19288 | 3/2001 |
| WO | 01/34066 | 5/2001 |
| WO | 01/34067 | 5/2001 |
| WO | 02/19949 | 3/2002 |
| WO | 03/015669 | 2/2003 |
| WO | 03/034949 A2 | 5/2003 |
| WO | 03/059208 | 7/2003 |
| WO | 03/075810 A1 | 9/2003 |
| WO | 2005/018504 | 3/2005 |
| WO | WO2005115278 A1 | 12/2005 |
| WO | 2007/040964 | 4/2007 |
| WO | 2007/067872 A2 | 6/2007 |
| WO | WO 2007-067872 | 6/2007 |
| ZA | 888414 | 10/1988 |

OTHER PUBLICATIONS

U.S. Appl. No. 10/280,937, filed Oct. 25, 2005.
Fechner et al. Iris-claw lens in phakic eyes to correct hyperopia: preliminary study. *J. Cataract Refract. Surg.*, 24, Jan. 1998.
Mandell, *Contact Lens Practice*, 4$^{th}$ Ed.
Menezo et al. Endothelial study of iris-claw phakic lens: four year follow-up. *J. Cataract Refract. Surg.*, 24, Aug. 1998.
Thornton, *Accommodation in Pseudophakia*, 25, p. 159.
AMO Specs, Model AC-21B, 1992.
Study Design of Nuvita, Mar. 20, 1997.
Program from ASCRS Symposium showing video tape between Apr. 10-14, 1999.
DVD titled "New elliptical accommodative IOL for cataract surgery" shown at ASCRS Symposium on Apr. 10, 1999.
U.S. Appl. No. 11/618,411—Pending claims submitted on Jul. 29, 2009.
U.S. Appl. No. 11/618,325—Pending claims submitted on Dec. 29, 2006.
English translation of WO 93/05733 A1.
U.S. Appl. No. 09/656,661 Filed Sep. 7, 2000.
U.S. Appl. No. 09/721,072, filed Nov. 22, 2000.

* cited by examiner

MULTIFOCAL ACCOMMODATING INTRAOCULAR LENS

RELATED APPLICATION

The present application claims priority under 35 U.S.C. §119(e) to provisional application No. 60/882,839, filed on Dec. 29, 2006.

BACKGROUND OF THE INVENTION

1. Field of the Invention

The present invention is directed to intraocular lenses, and more particularly to accommodating intraocular lenses having more than one focus or an extended depth of focus.

2. Description of the Related Art

A human eye can suffer diseases that impair a patient's vision. For instance, a cataract may increase the opacity of the lens, causing blindness. To restore the patient's vision, the diseased lens may be surgically removed and replaced with an artificial lens, known as an intraocular lens, or IOL. An IOL may also be used for presbyopic lens exchange or other elective ocular surgical procedures.

Monofocal IOLs have a single focal length, or, equivalently, a single power. Unlike the eye's natural lens, which can adjust its focal length within a particular range in a process known as accommodation, these single focal length IOLs cannot accommodate and provide clear vision only over a limited range of distances. As a result, distant objects may appear in focus, while objects at a normal reading distance from the eye may appear blurred.

Vision over a broader range of distances can be obtained either through the use of a multifocal lens, which provides different foci configured to produce focused images for different object distances, or an aspheric lens configured to provide an extended depth of focus or depth of field. While such lenses can improve the overall vision range, there may also be an associated reduction in visual acuity or overall visual quality.

Another approach is to use an accommodating IOL, which can adjust its axial position and/or optical power within a particular range, similar to the eye's natural lens. As a result, the patient can clearly focus on objects in a range of distances from the eye, rather than at a single distance. This ability to accommodate is of tremendous benefit for the patient, and more closely approximates the patient's natural vision than a single focal length IOL. One of the challenges in accommodating IOL's is providing a sufficient range of accommodation with the limited amount of ocular force available from the ciliary muscle. One solution to this problem is to combine an accommodating IOL with a multifocal or extended focus lens. Such approaches are disclosed in U.S. Pat. Nos. 6,503,276, 6,554,859, 6,638,305, and 7,018,409, which are herein incorporated by reference.

Another consideration is the location of the IOL within the eye. In the case of a pseudophakic eye, the IOL that replaces the eye's natural lens is commonly implanted within the capsular bag of the eye. The IOL has an optic, which refracts light that passes through it and forms an image on the retina, and a haptic, which mechanically couples the optic to the capsular bag. In the case of an accommodating IOL, the ciliary muscle and zonules exert a force on the capsular bag, which in turn exerts a force on the optic. The force may be transmitted from the capsular bag directly to the optic, or from the capsular bag through the haptic to the optic.

A desirable optic for an accommodating IOL is one that distorts in response to a squeezing or expanding radial force applied to the optic (i.e., by pushing or pulling on or near the edge of the optic, circumferentially around the optic axis). Under the influence of a squeezing force, the optic bulges slightly in the axial direction, producing more steeply curved anterior and/or posterior faces, and producing an increase in the power of the optic. Likewise, an expanding radial force produces a decrease in the optic power by flattening the optic. This change in power is accomplished in a manner similar to that of the natural eye and is well adapted to accommodation. Furthermore, this method of changing the lens power may reduce undesirable pressures exerted on some of the structures in the eye.

One challenge in implementing such an optic is designing a suitable haptic to couple the optic to the capsular bag. The haptic should allow distortion of the optic in an efficient manner, so that a relatively small ocular force from the ciliary muscle, zonules, and/or capsular bag can produce a relatively large change in power and/or axial location of the image. This may reduce fatigue on the eye, which is generally desirable.

Accordingly, there exists a need for an intraocular lens having a haptic with increased accommodative range and enhanced efficiency in converting a zonular force to a change in power and/or a change in axial location of the image. Better methods of implementing multifocal and extended focal IOL's into accommodating IOL's are also needed as a means for supplementing the overall accommodative range available to the eye.

SUMMARY OF THE INVENTION

Embodiments of the present invention are directed to devices and methods for providing accommodative vision. One aspect of the present invention involves an intraocular lens that comprises an adjustable optic and a haptic or mounting structure that is operably coupled to the optic. The adjustable optic comprises an optical axis, a central zone disposed about the optical axis, and an annular zone surrounding the central zone. The optic may also comprise additional annular zones disposed about the central zone and the first annular zone. The haptic comprises a transparent portion protruding into the adjustable optic. The intraocular lens has a disaccommodative configuration in which the central zone has a base optical power and an accommodative configuration in which the central zone has an add optical power that is at least about 1 Diopter greater than the base optical power, preferably at least about 2 Diopters greater than the base optical power, and even more preferably at least 3 Diopters, or even 4 Diopters, greater than the base optical power. The central zone and the annular zone have different optical powers when the adjustable intraocular lens is in the accommodative configuration and/or in the disaccommodative configuration.

As used herein "base optical power" or "base power" means power (in Diopters) of an IOL or other ophthalmic lens or lens system that is required to provide distant vision at the retina of a subject eye. As used herein "add optical power" or "add power" means a difference in power (in Diopters) between power required provide distant vision and the power of the lens portion having the add optical power. When the add optical power is a positive quantity, it is the difference in power between power required provide distant vision and the power required to focus light from an object at some finite distance from the eye. Alternatively, the add optical power may be a negative quantity.

In another aspect of the present invention, an intraocular lens comprises an adjustable optic and a haptic that is operably coupled to the optic. The optic comprises an optical axis, a central zone disposed about the optical axis, and an annular zone surrounding the central zone. The optic may also comprise additional annular zones disposed about the central zone and the first annular zone. The haptic comprises a transparent portion protruding into the adjustable optic. The intraocular lens has a natural configuration in which the central zone has a base optical power and a stressed configuration in which the central zone has an add optical power that is at least 1 to 4 Diopters greater than the base optical power. The central zone and the annular zone have different optical powers when the intraocular lens is in the stressed configuration and/or when the optic is in the natural configuration. Alternatively, the intraocular lens may have a natural configuration in which the central zone has the add optical power and a stressed configuration in which the central zone has a base optical power, wherein the add optical power is at least 1 to 4 Diopters greater than the base optical power.

In yet another aspect of the present invention, a method of providing accommodative vision to a subject comprises providing an intraocular lens according to an embodiment of the invention that includes an optic having a central zone and an annular zone surrounding the central zone. The method also comprises placing the intraocular lens into the eye of a subject in a disaccommodated configuration in which the central zone has a base optical power. The method further comprises adjusting the intraocular lens to an accommodated configuration in which the central zone has an add optical power that is at least 1 to 4 Diopters greater than the base optical power. The central zone and the annular zone simultaneously have different optical powers when the intraocular lens is in the accommodated configuration and/or when the optic is in the disaccommodative configuration. Alternatively, the intraocular lens may be placed into the eye in an accommodated configuration in which the central zone has the add optical power, wherein the intraocular lens is adjusted to a disaccommodated configuration in which the central zone has a base optical power that is suitable for providing intermediate and/or distant vision. In any event, when the intraocular lens is in the accommodated configuration, the central zone and/or surrounding zone is suitable for providing vision for objects that are relatively close to the subject (e.g., 12 to 24 inches from the subject) or objects at intermediate distances (e.g., 2 to 5 feet from the subject). When the intraocular lens is in the disaccommodated configuration, the central zone and/or surrounding zone is suitable for providing vision for objects that are distant (e.g., greater than 20 feet from the subject) and/or objects at intermediate distances.

BRIEF DESCRIPTION OF THE DRAWINGS

Embodiments of the present invention may be better understood from the following detailed description when read in conjunction with the accompanying drawings. Such embodiments, which are for illustrative purposes only, depict novel and non-obvious aspects of the invention. The drawings include the following figures.

DETAILED DESCRIPTION OF THE DRAWINGS

In a healthy human eye, the natural lens is housed in a structure known as the capsular bag. During natural accommodation, the capsular bag is driven by a ciliary muscle and zonular fibers (also known as zonules) in the eye, which can pull on the capsular bag to change its shape. The motion of the capsular bag generally deforms the natural lens in order to change its power and/or the location of the lens, so that the eye can focus on objects at varying distances away from the eye in a process known as accommodation. Embodiments of the present invention are directed to intraocular lenses that advantageously utilize the ocular forces produced by the ciliary muscle, zonules, and/or capsular bag to change the shape of the lens optic. Such an accommodating lens may produce vastly improved vision over a lens with a fixed power and location that does not accommodate. As used herein the term "ocular force" means a force that is sufficient to provide accommodation in the eye of a healthy human subject.

Figure 1:
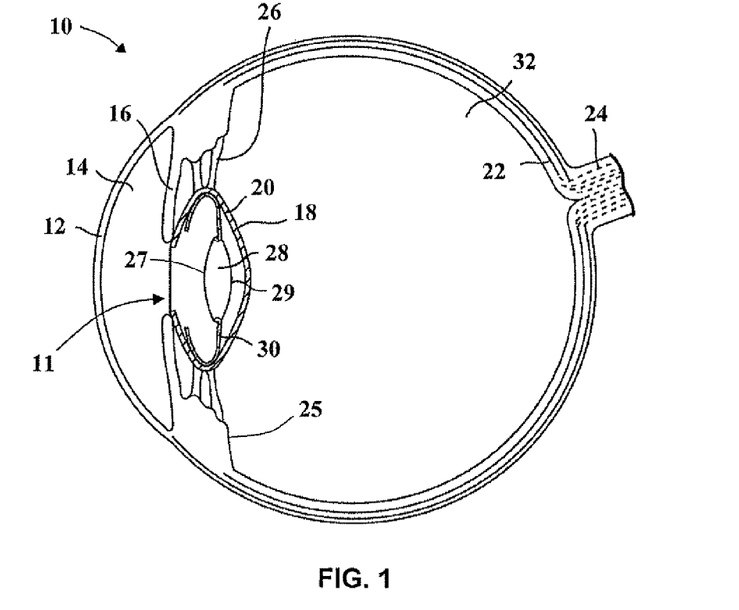
FIG. 1 is a plan drawing of a human eye having an implanted intraocular lens in an accommodative or "near" state.

FIG. 1 shows a human eye 10, after an accommodating intraocular lens 11, according to an embodiment of the present invention, has been implanted. Prior to surgery, the natural lens occupies essentially the entire interior of the capsular bag 18. After surgery, the capsular bag 18 may house the intraocular lens 11. Alternatively, the intraocular lens 11 may be configured to directly engage the zonules or ciliary muscle.

Light enters from the eye 10 from the left of FIG. 1 and passes through the cornea 12, the anterior chamber 14, the iris 16, and is directed onto the intraocular lens 11. After passing through the intraocular lens 11, light exits the posterior wall 20 of the capsular bag 18, passes through the posterior chamber 32, and strikes the retina 22, which detects the light and converts it to a signal transmitted through the optic nerve 24 to the brain.

A well-corrected eye forms an image at the retina 22. If the intraocular lens 11 has too much or too little power, the image shifts axially along the optical axis away from the retina, toward or away from the lens 11. Note that the total power of the eye (e.g., the combined power of cornea 12+intraocular lens 11) required to focus on a close or near object is more than the power required to focus on a distant or far object. The difference between the "near power" and "far power" is known typically as the range of accommodation or the add power. A typical range of accommodation or add power is about 2 to 4 diopters, but may be significantly larger for younger human subjects.

The intraocular lens 11 may be designed so that its relaxed or natural state is the "far" or "distant" condition (sometimes referred to as a "disaccommodative biased" intraocular lens), the "near" condition (an "accommodative biased" intraocular lens), or some condition in between the two. As used herein, the terms "natural state", "natural configuration", "relaxed state", and "relaxed condition" refer to a condition of an intraocular lens in which no external forces (e.g., ocular forces from the ciliary muscle, zonules, or capsular bag) are acting upon the intraocular lens 40 or haptic 44.

The capsular bag 18 is acted upon by the ciliary muscle 25 via the zonules 26, which distort the capsular bag 18 by stretching it radially in a relatively thick band about its equator. Experimentally, it is found that the ciliary muscle 25 and/or the zonules 26 typically exert a total force of up to about 10 grams of force, which is generally distributed uniformly around an equatorial region of the capsular bag 18. Although the range of ocular force may vary from patient to patient, the range of accommodation for each subject is generally limited by the total ocular force available. Therefore, it is generally preferred that the intraocular lens 11 be configured to vary its power over the full range of accommodation in response to this limited range of ocular forces (e.g., to provide at least 3 Diopters or 4 Diopters of accommodative power). In other words, it is desirable to have a relatively large change in power for a relatively small driving force. Alternatively, the effective range of accommodation may be increased by incorporating a lens having a multifocal or extended depth-of-focus configuration.

The intraocular lens 11 generally has two components: an optic 28 made of a transparent, deformable and/or elastic material, and a haptic 30 configured to hold the optic 28 in place and to mechanically transfers forces from the eye (e.g., from the capsular bag 18 or ciliary muscle 25) to the optic 28. The haptic 30 may have an engagement member with a central recess that is sized to receive the peripheral edge of the optic 28.

When the eye 10 is focused on a relatively close object, as shown in FIG. 1, the ciliary muscle 25 is compressed, which causes the zonules 26 to relax and allow the equatorial region of the capsular bag 18 to contract. The capsular bag 18 in this state is thicker at its center and has more steeply curved sides. As a result, the power of the lens is relatively high (e.g., the radii of curvature of one or both of the lens surfaces can decrease, and/or the lens can become thicker, and/or the lens can move axially), placing the image of the relatively close object at the retina 22. Note that if the lens could not accommodate, the image of the relatively close object would, for an emmetropic eye, be located behind the retina, and would appear blurred.

Figure 2:
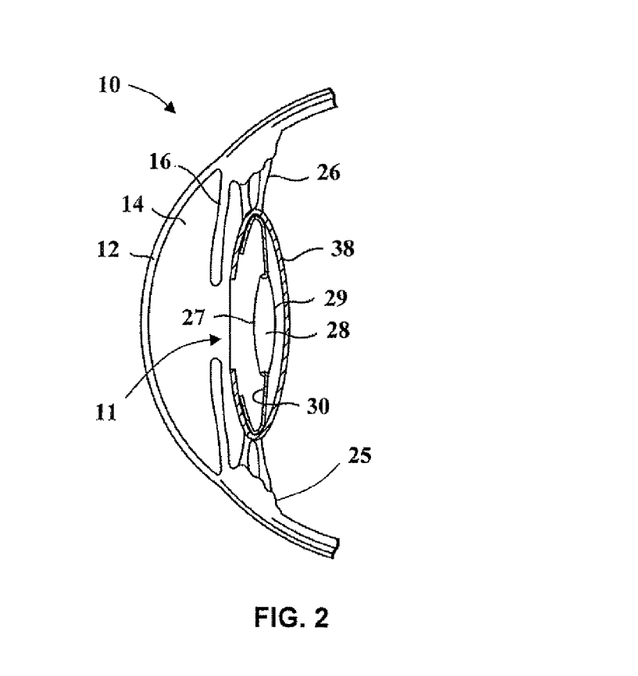
FIG. 2 is a plan drawing of the human eye of FIG. 1 in a disaccommodative or "far" state.
Figure 3:
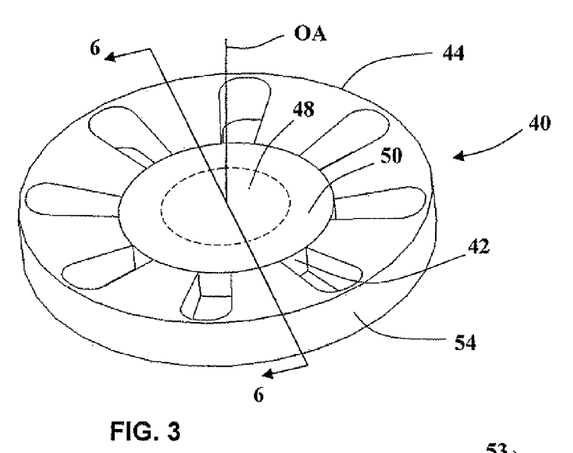
FIG. 3 is an isometric view of an intraocular lens according to a first embodiment of the invention showing an optic operably coupled to a haptic.
Figure 4:
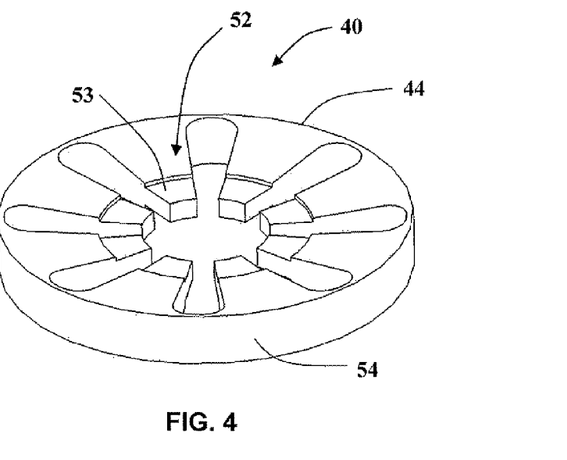
FIG. 4 is an isometric view of the haptic only from the intraocular lens shown in FIG. 3.
Figure 5:
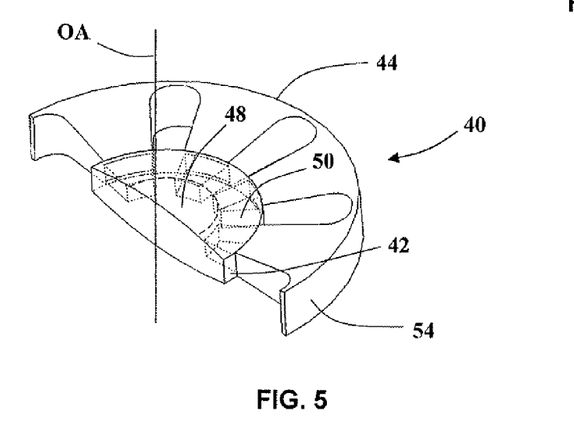
FIG. 5 is a cross-sectional isometric view of the intraocular lens of FIG. 3 showing a haptic segment operably coupled to an optic segment.

FIG. 2 shows a portion of the eye 10 focused on a relatively distant object. To focus on the distant object, the zonules 26 are retracted and the shape of the capsular bag 38 is thinner at its center and has less steeply curved sides. This reduces the lens power by flattening (i.e., lengthening radii of curvature and/or thinning) the lens, placing the image of the relatively distant object at the retina (not shown).

For both the "near" case of FIG. 1 and the "far" case of FIG. 2, the accommodating intraocular lens deforms and changes shape in response to the ciliary muscle 25 and/or to the distortion of the capsular bag 18. For the "near" object, the haptic 30 compresses the optic 28 at its edge, increasing the thickness of the optic 28 at its center and more steeply curving its anterior face 27 and/or its posterior face 29. As a result, the lens power increases. For the "far" object, the haptic 30 expands, pulling on the optic 28 at its edge, and thereby decreasing the thickness of the optic 28 at its center and less steeply curving (e.g., lengthening one or both radius of curvature) its anterior face 27 and/or its posterior face 29. As a result, the lens power decreases.

Note that the specific degrees of change in curvature of the anterior and posterior faces 27, 29 depend on the nominal curvatures. Although the optic 28 is drawn as bi-convex, they may also be plano-convex, meniscus or other lens shapes. In all of these cases, the optic 28 is compressed or expanded by forces from the haptic to the edge and/or faces of the optic 28. In addition, there may be some axial movement of the optic 28. In some embodiments, the haptic 30 is configured to transfer the generally symmetric radial forces symmetrically to the optic 28 to deform the optic 28 in a spherically symmetric way. However, in alternate embodiments the haptic 30 is configured non-uniformly (e.g., having different material properties, thickness, dimensions, spacing, angles or curvatures), to allow for non-uniform transfer of forces by the haptic 30 to the optic 28. For example, this could be used to compensate for astigmatism, coma or other asymmetric aberrations of the eye/lens system. The optics 28 may optionally have one or more diffractive, multifocal, and/or aspheric elements or surfaces.

Referring to FIGS. 3-7, in certain embodiments, an intraocular lens 40 comprises an adjustable optic 42 and a haptic 44. The optic 42 has a clear aperture 43 that includes an anterior surface 45 and a posterior surface 46. The clear aperture includes a central zone 48 disposed about an optical axis OA and a surrounding or annular zone 50 surrounding the central zone 48.

The haptic 44 may comprise a plurality of arms 52 that protrude into the adjustable optic 42 and into the clear aperture 43. In order to provide a large clear aperture, the haptic 44 and arms 52 includes transparent portions 53 that protrude into the adjustable optic 42 and into the clear aperture 43. The haptic 44 and arms 52 generally protrude into the annular zone 50 but may also partially protruded into the central zone 48. The haptic 44 and arms 52 are configured to deform the central zone 48 in response to an ocular force from the ciliary muscle and/or capsular bag, thereby changing the power of the central zone 48 by at least 1 Diopter, preferably by at least 2 Diopters or at least 4 Diopters. By contrast the annular zone 50 does not change shape in response to an ocular force or changes shape by an amount that produces less accommodative power change than the power change of the central zone 48 (e.g., changes power by less than 1 Diopter in response to an ocular force, less than 0.5 Diopters in response to an ocular force, or less than 0.25 Diopters in response to an ocular force).

The transparent portion 53 preferably has a transmissivity of at least about 80%, more preferably of at least 90% or even 95%. In some embodiments, the haptic 44 is made of a material that has a refractive index that is substantially equal to the refractive index of the optic 42, thus reducing or eliminating glare and aberration problems that could be introduced by a mismatch in refractive indices. For the purposes of this document, "essentially the same", "essentially equal", or "substantially equal" may mean that their refractive indices are equal to each other at a wavelength within the visible spectrum (i.e., between 400 nm and 700 nm). Note that the haptic and optic may optionally have different dispersions, where the refractive index variation, as a function of wavelength, may be different for the haptic and the optic. In other words, if the refractive indices of the haptic and optic are plotted as a function of wavelength, they may or may not have different slopes, and if the two curves cross at one or more wavelengths between 400 nm and 700 nm, then the refractive indices may be considered to be essentially the same or essentially equal.

As used herein, the term "clear aperture" means the opening of a lens or optic that restricts the extent of a bundle of light rays from a distant source that can imaged or focused by the lens or optic. The clear aperture is usually circular and specified by its diameter. Thus, the clear aperture represents the full extent of the lens or optic usable for forming the conjugate image of an object or for focusing light from a distant point source to a single focus or to a plurality of predetermined foci, in the case of a multifocal optic or lens. It will be appreciated that the term clear aperture does not limit the transmittance of lens or optic to be at or near 100%, but also includes lenses or optics having a lower transmittance at particular wavelengths or bands of wavelengths at or near the visible range of the electromagnetic radiation spectrum. In some embodiments, the clear aperture has the same or substantially the same diameter as the optic 42. Alternatively, the diameter of the clear aperture may be smaller than the diameter of the optic 42, for example, due to the presence of a glare or PCO reducing structure disposed about a peripheral region of the optic 42.

Figure 6:
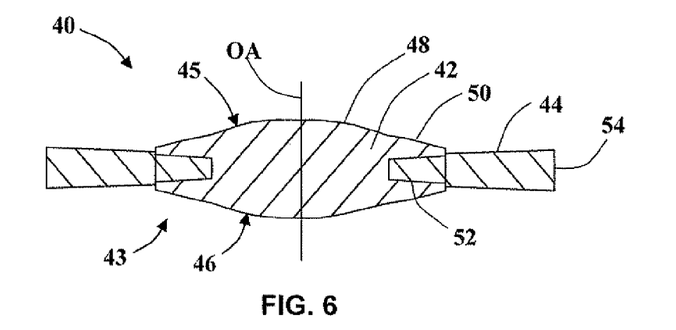
FIG. 6 is a cross-sectional view through the section 6-6 of FIG. 3 showing a portion of a haptic protruding into an optic and the intraocular lens in a disaccommodative state.
Figure 7:
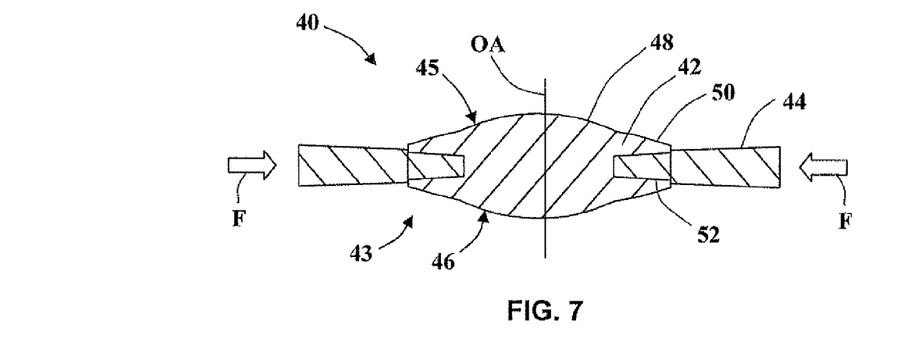
FIG. 7 is a cross-sectional view of the intraocular lens shown in FIG. 6 in an accommodative state.

The intraocular lens 40 and the optic 42 may be adjusted between an accommodative state and a disaccommodative state. For example, referring to FIG. 6, the optic 42 has a disaccommodative configuration or state in which the central zone 48 has a base optical power suitable for distant vision. Referring to FIG. 7, the intraocular lens 40 has an accommodative configuration or state in which the central zone 48 has an add optical power suitable for near or intermediate vision. The base optical power is generally selected to provide a subject with distant vision (e.g., for objects at distances greater than 20 feet from the subject), while the add optical power of central zone 48 may be exploited to provide a subject with better vision for near objects (e.g., for objects at distances between 12 to 24 inches from the subject) and/or intermediate distances (e.g., for objects at distances between 2 to 5 feet from the subject). Accordingly, the add power is preferably at least about 1 Diopter greater than the base optical power, more preferably at least 2 Diopters greater than the base optical power, and even more preferably at least 3 Diopters or 4 Diopters greater than the base optical power. In the illustrated embodiment, the add optical power is produced by the decreasing radius of curvature of the anterior and posterior surfaces 45, 46, as illustrated by comparing FIG. 7 to FIG. 6. In some embodiments, the optical add power may be supplemented by accommodative movement of the optic 40 in the anterior direction (e.g., away from the retina of the eye). While the add optical power will generally comprises a positive change in the accommodative power, the add optical power may alternatively be a negative add power.

In certain embodiments, the surrounding zone 50 also has a base optic power when the intraocular lens 40 is in a disaccommodative state and an add optical power when the intraocular lens 40 is in an accommodative configuration. The add optical power of the surrounding zone 50 may be equivalent to the add optical power of the central zone 48. Alternatively, the add optical power of the surrounding zone 50 may be greater than or less than the add optical power of the central zone 48. This difference in the add power between the central and surrounding zones 48, 50 may be the result of differences in how forces on the haptic 44 are transferred to the zones 48, 50.

In addition to providing accommodative power, the central and annular zones 48, 50 generally combine to provide a multifocal lens when the intraocular lens is in the accommodative state, the disaccommodative states, and/or at intermediate states therebetween. Thus, for any given state or configuration of the central and annular zones 48, 50, the intraocular lens 40 may be configured to generally provide an extended depth of focus or multiple foci that allows resolution of objects at varying distances (e.g., simultaneously providing near and intermediate vision, or simultaneously providing intermediate and distant vision).

The multifocality of the intraocular lens 40 (e.g., the differences in optical power of the central and surrounding zones 48, 50) may be produced by a radius of curvature between the anterior and/or posterior surfaces 45, 46 of the central zone 48 and the surrounding zone 50. For example, referring to FIGS. 6 and 7, the radius of curvature of the anterior and posterior surfaces 45, 46 in the region of central zone 48 is less than the radius of curvature of those surfaces in the region of the surrounding zone 50, both in the accommodative state (FIG. 6) and disaccommodative state (FIG. 7). It will be appreciated that the difference in the radius curvatures in the central and annular zones 48, 50 have been exaggerated for illustrative purposes. In some embodiments, the larger radius of curvature in the surrounding zone 50 is selected to provide distant vision, while the smaller radius of curvature of the central zone 48 is selected to provide a larger optical power suitable for intermediate vision and/or near vision. In some embodiments, the difference in optical power of the two zones 48, 50 is at least partially provided by a diffractive grating or phase plate that is placed on one or both surfaces of the central zone 48 and/or the surrounding zone 50.

In the illustrated embodiment, the central zone 48 has a greater optical power than the surrounding zone 50. Alternatively, the central zone 48 may have the same or less optical power than the surrounding zone 50 when the intraocular lens 40 is in the accommodative configuration, the disaccommodative configuration, or in some state between the accommodative and disaccommodative configurations. In some embodiments, the zones 48, 50 are configured to have the same optical power (e.g., to be a monofocal lens having substantially a single focus) when the intraocular lens 40 is in either the accommodative state or disaccommodative state. Alternatively, the zones 48, 50 may be configured to have the same optical power at an intermediate state of the intraocular lens 40 and different optical powers when the intraocular lens 40 is in either the accommodative state or disaccommodative state.

The diameter of central and surrounding zones 48, 50 may selected to provide a predetermined mix of near, distant, and/or intermediate vision that varies as a function of lighting conditions (e.g., as a function of the amount of the optic 42 exposed as the iris of the varies in size). For example, diameter of the central zone 48 may be at least about 2-millimeters. Alternatively, the diameter of the central zone 48 may be greater than 3 millimeters or greater than 4 millimeters. In some embodiments, the outer diameter of the surrounding zone is greater than about 4 millimeters, preferably greater than or equal to 5 millimeters or greater than or equal to 6 millimeters. In certain embodiments, the optic 42 comprises one or more additional zones surrounding the zones 48, 50, for example, to further adjust the mixture of near, distant, and/or intermediate vision as a function of lighting conditions. In some embodiments, the optic 42 further comprises an intermediate or transition zone disposed between the central and surrounding zones 48, 50 that is configured, for example, to preclude discontinuities between the zones 48, 50 that could produce glare or other unwanted optic effects.

In some embodiments, the central zone 48 and/or the surrounding zone 50 has at least one surface 45, 46 that is aspheric and/or toric in shape and that may be configured to correct an aberration of the eye (e.g., astigmatism, spherical aberrations, coma, and the like). The aspheric or toric shape and associated correction may be present when the intraocular lens 40 is in the accommodative configuration, the disaccommodative configuration, or both the accommodative and disaccommodative configurations. The central zone 48 and/or the surrounding zone 50 may comprises a diffractive grating or phase plate that is configured to increase or decrease the optical power of the one zone as compared to the remaining zone (which may also include a diffractive zone or grating having a different power). In some embodiments, the diffractive grating or phase plate may be configured to correct for a chromatic aberration.

The optic 42 and the haptic 44 may be integrally made of a single material. Alternatively, the optic 42 may be made of material from one family and the haptic 44 may be made of material from another family (e.g., one from an acrylic family member and the other from a silicone family member). One or both of the optic 42 and the haptic 44 may be made of a hydrophilic material. In some embodiments, the intraocular lens 40 is fabricated such that the optic 42 is stressed by the haptic 44 when the intraocular lens 40 is in a natural state in which there are no external forces acting on the intraocular lens 40. Examples of this type of pre-stressing of an optic are discussed in co-pending U.S. patent application Ser. No. 11/618,411, which is herein incorporated by reference. Other haptic configurations may be incorporated into embodiments of the present invention such as, for examples, those discussed in co-pending U.S. patent application Ser. No. 11/618,325, which is herein incorporated by reference.

The optic 42 may be made from a relatively soft material and configured so that at least a portion of the optic 42 distorts or changes shape readily under the limited deforming force initiated by the ciliary muscle and/or capsular bag and transmitted through the haptic 44. An exemplary material is a relatively soft silicone material, although other suitable materials may be used as well. The stiffness of the optic 42 may be less than 500 kPa, or preferably may be between 0.5 kPa and 500 kPa, or more preferably may be between 10 kPa and 200 kPa, or even more preferably may be between 10 kPa and 50 kPa or between 25 kPa and 50 kPa. In contrast with the optic 42, the haptic 44 may be made from a relatively stiff material, so that it can efficiently transmit the deforming forces from the capsular bag to the optic 42. An exemplary material is a relatively stiff silicone material, although other suitable materials may be used as well, such as acrylic, polystyrene, or clear polyurethanes. The haptic 44 may preferably be stiffer than the optic 42. The stiffness of the haptic 44 may be greater than 500 kPa, or preferably may be greater than 3000 kPa.

Various types of materials, haptic configurations, and/or optic configurations may be utilized to provide a predetermined amount of optic distortion or shape change in response to an ocular force, either to the optic 42 or to any other optic embodiment discussed or suggested herein. Examples of such materials and mechanisms for providing a desired amount of optic shape change or distortion due to ocular forces may be found in U.S. Pat. No. 7,125,422 and in US Patent Application Numbers 2004/0082993, 2004/0111153, and 2005/0131535, all of which are herein incorporated by reference in their entirety. As an example, the optic 42 may comprise an optic body and a liquid or gel material disposed within a void of the optic body. Such an optic structure may be configured to both provide a low optic stiffness and to maintain an overall optic shape that is suitable for vision.

Figure 8:
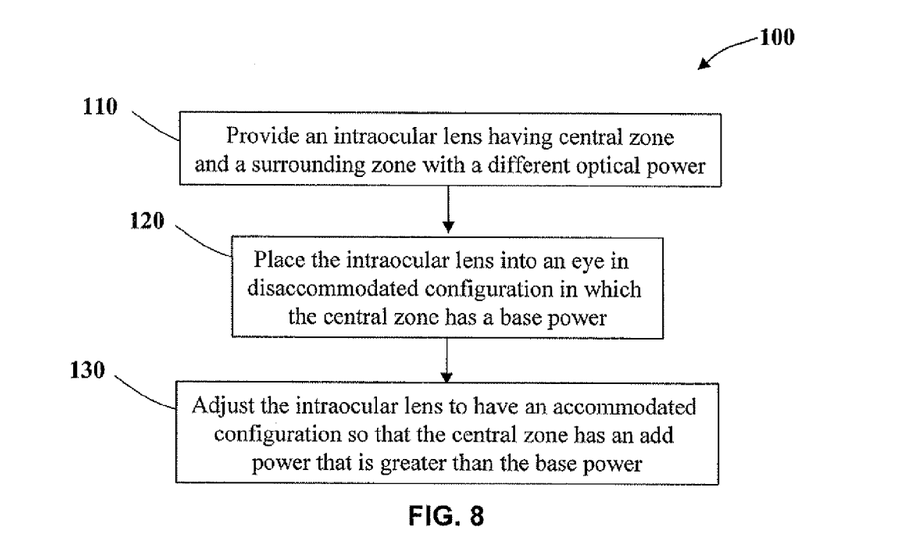
FIG. 8 is a block diagram of a method implanting an intraocular lens and providing accommodative vision.

In certain embodiments, a method 100 of implanting an intraocular lens and providing accommodative vision to a subject comprises an operational block 110 of providing the intraocular lens 40 having a central zone 38 and a surrounding zone 40. The method also comprises an operational block 120 of placing the intraocular lens 40 into the eye of a subject in a disaccommodated configuration in which the central zone has a base optical power. The method 100 further comprise an operational block 130 of adjusting or causing the intraocular lens to have an accommodated state within the eye, wherein the central zone 48 has an add optical power that is at least 1 Diopter greater than the base optical power, preferably 2 Diopters greater than the base optical power, and even more preferably 3 to 4 Diopters greater than the base optical power. Generally the central zone 48 and the surrounding zone 50 simultaneously have different optical powers when the optic 42 is in the accommodated configuration and/or when the optic 42 is in the disaccommodative configuration.

The method 100 is generally used in conjunction with an intraocular lens having a disaccommodative bias. For example, the intraocular lens 42 may be configured to have a disaccommodative bias such that the surrounding zone 40 has an optical power that is selected to provide distant vision when the intraocular lens 40 is in a natural configuration in which there are no external forces on the haptic 44. Thus, when the intraocular lens 40 is placed into the eye 10, it has a relatively elongate shape in a direction that is perpendicular to the optical axis OA, as illustrated in FIG. 6.

In operational block 130, the intraocular lens is adjusted to have an accommodative configuration as an ocular force F (illustrated in FIG. 7) radially pushes the haptic 44 toward the optical axis OA. This places the intraocular lens 40 in a stressed state or configuration so that the adjustable optic 42 deforms and/or thickens into a more oval shape that will increase the optical power of the central zone 48 and optionally increase the optical power of the surrounding zone 50. The ocular force F is typically within a range of at least about 1 gram to about 10 grams, preferably within a range of 5 to 10 grams. In some embodiments, the ocular force is relatively small, for example, within a range of about 1 to 5 gram or about 1 to 3 grams. Within the art, an understanding of the physiology of the eye is still developing. Thus, other ranges of ocular forces able to provide the above ranges of relative and/or absolute thickness change are anticipated as the physiology of the eye is better understood. Such ranges of ocular forces are also consistent with embodiments of the present invention as disclosed herein.

The intraocular lens 40 may be placed in the capsular bag 18 of the eye 10, such that an outer periphery 54 of the haptic 44 is in contact with an equatorial region of the capsular bag 18. In such embodiments, a contraction of the ciliary muscle 25 causes the capsular bag 18 to produce the ocular force F, causing the intraocular lens 40 into the accommodating configuration. Alternatively, the intraocular lens 40 may be configured for placement in another portion of the eye 10. For example, the intraocular lens 40 may be configured for placement in front of the capsular bag 18 so that the haptic 44 is in direct contact with the ciliary muscle 25 or even the zonules 26.

Referring to FIGS. 9-12, an intraocular lens 240 comprising an adjustable optic 242 and a haptic 244 may be configured to have a disaccommodative bias when placed into the eye 10. The optic 242 includes a central zone 248 and a surrounding zone 250 that are similar to the zones 48, 50, respectively. The intraocular lens 240 is similar to the intraocular lens 40 with at least the exception that it includes an inner ring 246. At least a portion of the inner ring 246 is transparent and has a transmissivity of at least 80%, preferably at least 90% or even 95%. The haptic 244 further comprises a plurality of arms 252 that connect the inner ring 246 with the peripheral portion 251. In the illustrated embodiment, there are eight arms 252; however, more or fewer arms may be used (e.g., 4 arms or 16 arms).

The inner ring 246 is configured to deform an optic 242 in response to an ocular force acting on a peripheral portion 251 of the haptic 244. The inner ring 246 is shown in the form of a contiguous ring in FIGS. 9 and 11. Alternatively, the inner ring 246 may be in the form of a broken ring with radial voids between ring segment, for example, with a radial void disposed between each of the arms 252. The peripheral portion 251 may be in the form of a contiguous ring, as shown in the illustrated embodiment, or in the form of a broken ring. Either or both rings 246, 251 may have shapes that are not circular and may be shaped to distribute an ocular force about the optic 242 in a predetermined manner.

Figure 9:
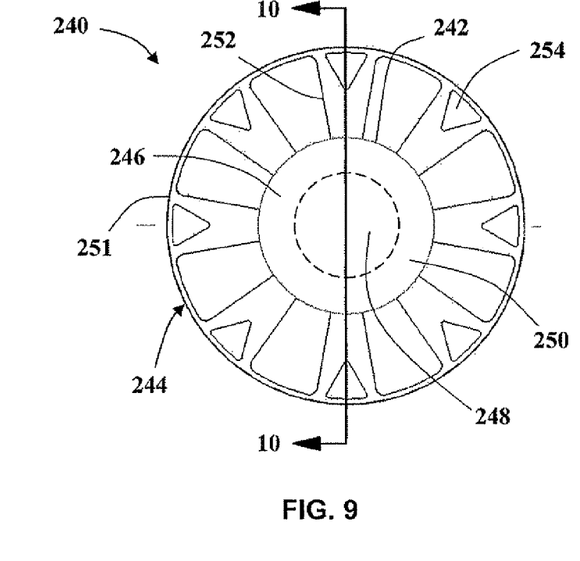
FIG. 9 is a front view of an intraocular lens according to a second embodiment of the invention.
Figure 11:
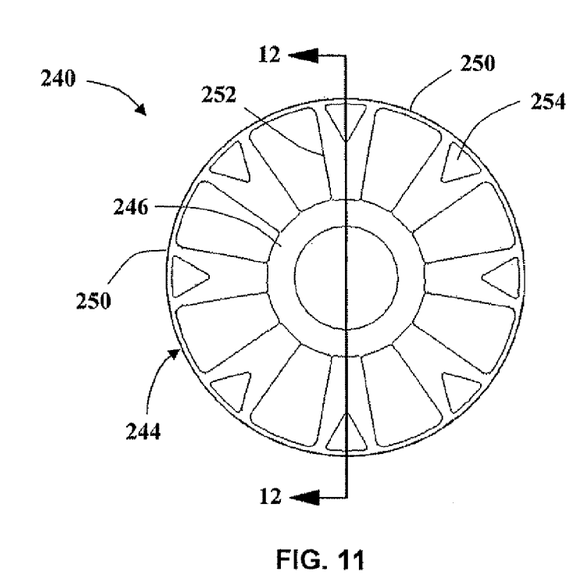
FIG. 11 is a front view of the haptic only from the intraocular lens shown in FIG. 9.
Figure 12:
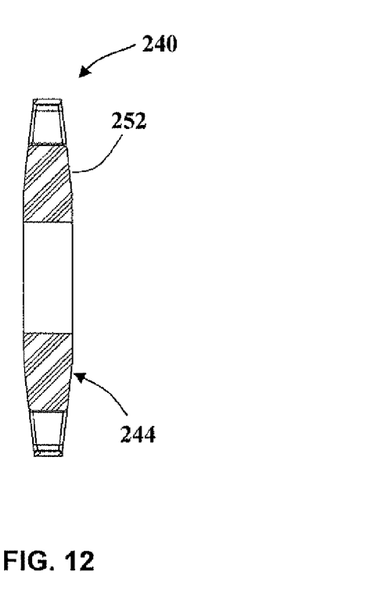
FIG. 12 is a cross-sectional view through the section 12-12 of FIG. 11.

The arms 252 may include void portions 254 configured to reduce the mass of the intraocular lens 240 and the haptic 244. Such reduction in mass may be utilized to allow the ocular force F to be more completely transmitted to the inner ring 246 and optic 242. The void portions may be triangular in shape, as illustrated in FIGS. 9 and 11, or may have some other shape (e.g., circular or rectangular) that may be selected to provide a desired mass reduction and/or distribution of forces on the inner ring 246 and/or adjustable optic 242.

Figure 10:
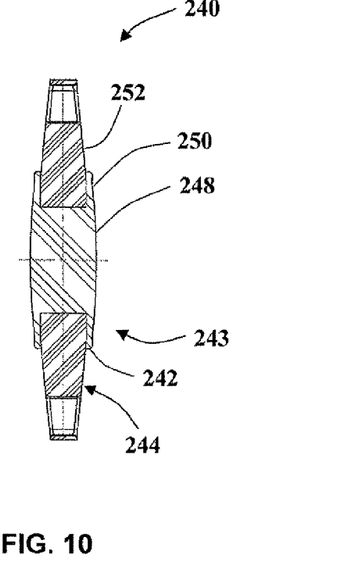
FIG. 10 is a cross-sectional view through the section 10-10 of FIG. 9.

The thickness along the optical axis OA of inner ring 246 (and/or of portions of the haptic 244 disposed within the adjustable optic 242) may be selected to control the amount and/or distribution of an ocular force acting on the intraocular lens 240. For example, in some embodiments, the performance (e.g., the change Diopter power of the intraocular lens 240 between accommodative and disaccommodative configurations) increases as the edge thickness increases. In such embodiments, other design constraints (e.g., optical performance or physical constraints of the eye) may, however, place an upper limit on the maximum optic edge thickness. In some embodiments, the ring portion 246 of the haptic 244 has a maximum axial thickness that is at least one half a maximum axial thickness of the central zone, as illustrated in FIG. 10. In other embodiments, the ring portion 246 of the haptic 244 has a maximum axial thickness that is at least 75% of a maximum axial thickness of the central zone. These and other predetermined relationships between axial thicknesses of the protruding portions of the haptic 244 and the axial thicknesses of the optic 242 may also be advantageously applied to other embodiments of the invention discussed or suggested herein. Also, where applicable, any of the features, limits, and so forth disclosed with regard to the intraocular lens 40 may also be applied to the intraocular lens 240.

Figure 13:
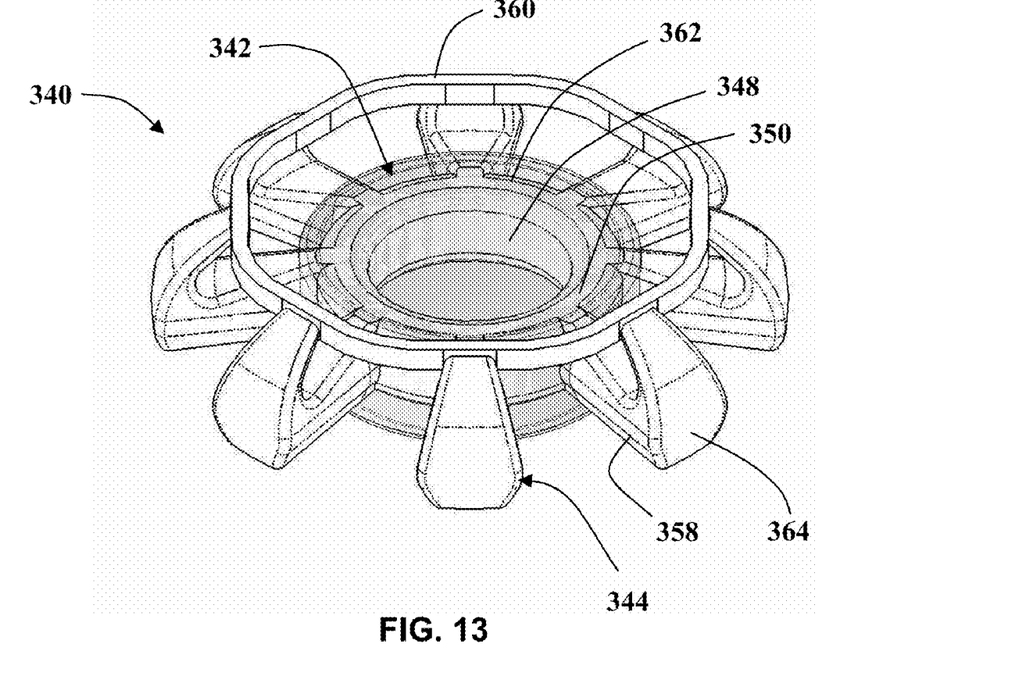
FIG. 13 is an isometric view of an intraocular lens according to a third embodiment of the invention.
Figure 14:
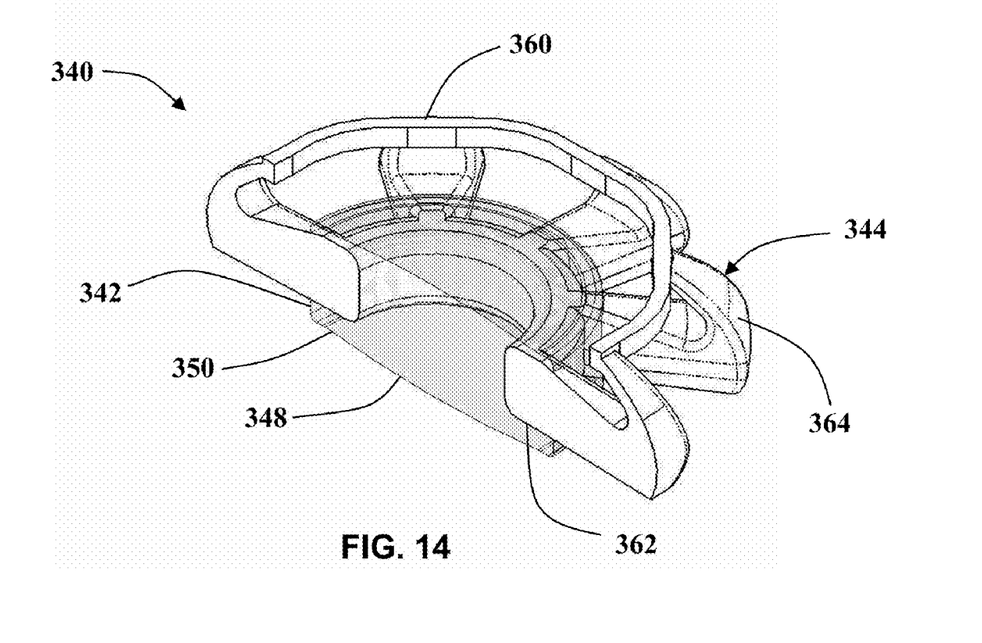
FIG. 14 is a cross-sectional isometric view of the intraocular lens of FIG. 13 showing a haptic segment operably coupled to an optic segment.
Figure 15:
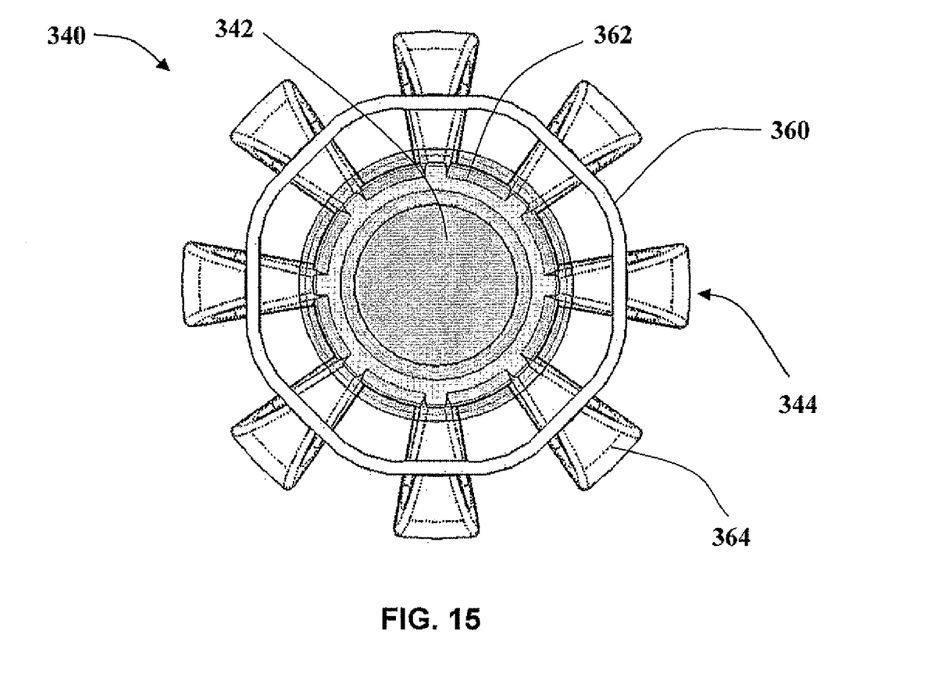
FIG. 15 is a front view of the intraocular lens shown in FIG. 13

Referring to FIGS. 13-15, an intraocular lens 340 comprising an adjustable optic 342 and a haptic 344 may be configured to have an accommodative bias when placed into the eye 10. The optic 342 includes a central zone 348 and a surrounding zone 350 that are similar to the zones 48, 50, respectively, of the previous embodiment. The haptic 344 comprises a plurality of arms 358 connected together at their distal ends by an external ring 360 and at their proximal ends by an inner ring 362 disposed within the optic 342. In the illustrated embodiment, there are eight arms 358; however, more or fewer arms may be used. Similar to the intraocular lens 240, at least a portion of the ring 362 is transparent and has a transmissivity of at least about 80%, preferably at least 90% or even 95%. Preferably, the refractive index of the inner ring is substantially the equal to the refractive index of the adjustable optic 342.

In contrast to the intraocular lens 240, the outer surface of the haptic 344 is configured to contact a relatively larger region of a capsular bag 18, for example, a region that extends beyond an equatorial region of the capsular bag 18. In the illustrated embodiment, the haptic comprises an outer surface 364 that is configured to conform to at least one of the anterior and posterior capsules of a capsular bag into which the intraocular lens is placed. The relatively large surface area of the outer surface 364 of the haptic 344 may be utilized to provide increased adhesion between the capsular bag and the intraocular lens 340.

Because of this increased adhesion, the intraocular lens 340 may be better suited for use as an accommodatively biased intraocular lens or other configurations where the intraocular lens is pulled outwardly by the capsular bag. In certain embodiments, a method implanting the intraocular lens 340 and providing accommodative vision is similar to that of the method 100, except that the intraocular lens 340 is placed into the eye in an accommodated configuration and adjusted to a disaccommodative configuration by using the walls of a capsular bag to pull radially outward on the inner ring 362 and the adjustable optic 342. Where applicable, any of the features, limits, and so forth disclosed with regard to the intraocular lenses 40, 240 may also be applied to the intraocular lens 340.

The description of the invention and its applications as set forth herein is illustrative and is not intended to limit the scope of the invention. Variations and modifications of the embodiments disclosed herein are possible, and practical alternatives to and equivalents of the various elements of the embodiments would be understood to those of ordinary skill in the art upon study of this patent document. These and other variations and modifications of the embodiments disclosed herein may be made without departing from the scope and spirit of the invention.

What is claimed is:

1. An intraocular lens, comprising:
an adjustable optic disposed about an optical axis comprising a central zone disposed about the optical axis and an annular zone surrounding the central zone; and
a haptic comprising a plurality of arms coupled at a first end with a first ring segment, the arms coupled at a second end with a second ring segment, the second end of the arms being disposed between the first end of the arms and the optical axis, wherein the haptic includes a transmissive portion that protrudes within the adjustable optic;
the intraocular lens having a disaccommodative configuration in which the central zone has a base optical power and an accommodative configuration in which the central zone has an optical power that is equal to the base optical power plus an add optical power.

2. The intraocular lens of claim 1, wherein the intraocular lens is configured to produce one of the lens configurations in response to an ocular force produced by the eye of a subject into which the intraocular lens is placed.

3. The intraocular lens of claim 2, wherein the ocular force is less than about 6 grams.

4. The intraocular lens of claim 2, wherein the ocular force is produced by a deformation of the capsular bag of the eye.

5. The intraocular lens of claim 1, wherein the add optical power is at least 3 Diopters.

6. The intraocular lens of claim 1, wherein the intraocular lens has a disaccommodative bias in which the intraocular lens has the disaccommodative configuration when the lens is in a natural state.

7. The intraocular lens of claim 1, wherein the optical power of the central zone, for at least one of the lens configurations, is greater than the optical power of the annular zone.

8. The intraocular lens of claim 1, wherein the add power of central zone is at least 3 Diopters greater than the base optical power thereof.

9. The intraocular lens of claim 1, wherein the second ring segment has a maximum axial thickness that is at least one half a maximum axial thickness of the central zone.

10. The intraocular lens of claim 1, wherein the protruding portion of the haptic has a refractive index that is equal to a refractive index of the adjustable optic at a wavelength within the visible spectrum.

11. The intraocular lens of claim 1, wherein the first segment is configured to conform to at least one of the anterior capsule and the posterior capsule of a capsular bag into which the intraocular lens is placed.

12. The intraocular lens of claim 1, wherein the protruding portion of the haptic protrudes into the edge of the adjustable optic.

13. The intraocular lens of claim 1, wherein the haptic is stiffer than the adjustable optic.

14. The intraocular lens of claim 1, wherein the haptic comprises at least two materials having different stiffnesses.

15. The intraocular lens of claim 1, wherein the adjustable optic comprises a material having a stiffness that is less than 50 kPa.

16. The intraocular lens of claim 1, wherein the adjustable optic comprises a material having a stiffness that is less than 100 kPa.

17. The intraocular lens of claim 1, wherein the second segment is a part of a second ring.

18. The intraocular lens of claim 17, wherein the second ring comprises voids between two adjacent arms.

19. The intraocular lens of claim 1, wherein the first ring segment is a part of a first ring.

20. The intraocular lens of claim 1, wherein the add optical power is at least 1 Diopter.

21. The intraocular lens of claim 1, wherein the central zone and the annular zone simultaneously have different optical powers when the adjustable intraocular lens is in one of or both the accommodative configuration and the disaccommodative configuration.

22. The intraocular lens of claim 1, wherein the portion of the haptic that protrudes within the adjustable optic includes the second ring segment.

23. The intraocular lens of claim 1, wherein at least one of the plurality of arms includes a void.

24. An intraocular lens, comprising:
an adjustable optic disposed about an optical axis comprising a central zone disposed about the optical axis and an annular zone surrounding the central zone; and
a haptic including a plurality of arms connected together at their distal ends by a first ring disposed adjacent an outer periphery of the intraocular lens and at their proximal ends by a second ring, wherein at least one of the plurality of arms includes a void;
the intraocular lens having a natural configuration in which the central zone has a first optical power and a stressed configuration in which the central zone has a second optical power;
wherein the second ring is engaged with the adjustable optic.

25. The intraocular lens of claim 24, wherein the intraocular lens has a disaccommodative bias.

26. The intraocular lens of claim 24, wherein the second optical power differs from the first optical power by at least 1 Diopter.

27. The intraocular lens of claim 24, wherein the central zone and the annular zone simultaneously have different optical powers when the intraocular lens is in one of or both the stressed configuration and the natural configuration.

28. The intraocular lens of claim 24, wherein the first ring is spaced apart from the optic by the plurality of arms along a direction perpendicular to the optical axis.

29. A method of providing accommodative vision to a subject, comprising:
providing an intraocular lens comprising:
an adjustable optic disposed about an optical axis, the optic comprising a central zone disposed about the optical axis and an annular zone surrounding the central zone; and
a haptic including a plurality of arms protruding inside the adjustable optic, at least some of the plurality of arms being connected at their proximal ends by a ring segment disposed within the adjustable optic;
the intraocular lens having a disaccommodative configuration in which the central zone has a base optical power and an accommodative configuration in which the central zone has an optical power that is equal to the base optical power plus an add optical power;
placing the intraocular lens into the eye of a subject in the disaccommodated configuration in which the central zone has the base optical power.

30. The method of claim 29, wherein the add optical power is greater than or equal to 1 Diopter.

31. The method of claim 29, wherein the central zone and the annular zone simultaneously have different optical powers when the intraocular lens is in one of or both the accommodated configuration and the disaccommodative configuration.

32. An intraocular lens, comprising:
an adjustable optic disposed about an optical axis comprising a central zone disposed about the optical axis and an annular zone surrounding the central zone; and
a haptic including a plurality of arms connected together at their proximal ends by an inner peripheral structure, the inner peripheral structure located inside the adjustable optic;
the intraocular lens having a first configuration in which the central zone has a first optical power and a second configuration in which the central zone has second optical power that differs from the first optical power, at least one of the first and second configurations being induced by deformation of the adjustable optic by the inner peripheral structure in response to ocular forces transmitted by the arms.

33. The intraocular lens of claim 32, wherein the add power of central zone is greater than or equal to 3 Diopters.

34. The intraocular lens of claim 32, wherein the inner peripheral structure has a refractive index that is equal to a refractive index of the adjustable optic at one wavelength within the visible spectrum.

35. The intraocular lens of claim 32, wherein the central zone and the annular zone simultaneously having unequal optical powers from one another when the adjustable intraocular lens is in the first configuration, when the adjustable, intraocular lens is in the second configuration, or when the adjustable intraocular lens is in the first configuration and when the adjustable intraocular lens is in the second configuration.

36. The intraocular lens of claim 32, wherein the second optical power differs from the first optical power by an amount that is greater than or equal to 1 Diopter.

* * * * *